United States Patent
Gregoire et al.

(10) Patent No.: US 12,023,019 B2
(45) Date of Patent: Jul. 2, 2024

(54) TISSUE REPAIR ASSEMBLY AND SYSTEM WITH SOFT ANCHORING IMPLANT

(71) Applicant: Smith & Nephew, Inc., Memphis, TN (US)

(72) Inventors: David Gregoire, Mission Viejo, CA (US); Vincent Tangherlini, Rancho Santa Margarita, CA (US); Ian Lo, Calgary (CA); Christopher Rodriguez, Costa Mesa, CA (US); Tri Nguyen, Garden Grove, CA (US)

(73) Assignee: Smith & Nephew, Inc., Memphis, TN (US)

( * ) Notice: Subject to any disclaimer, the term of this patent is extended or adjusted under 35 U.S.C. 154(b) by 130 days.

(21) Appl. No.: 17/821,573

(22) Filed: Aug. 23, 2022

(65) Prior Publication Data

US 2022/0395267 A1 Dec. 15, 2022

Related U.S. Application Data

(63) Continuation of application No. 16/342,877, filed as application No. PCT/US2017/059943 on Nov. 3, 2017, now Pat. No. 11,452,516.
(Continued)

(51) Int. Cl.
*A61B 17/04* (2006.01)
*A61F 2/08* (2006.01)
*A61B 17/00* (2006.01)

(52) U.S. Cl.
CPC ........ *A61B 17/0401* (2013.01); *A61F 2/0811* (2013.01); *A61B 2017/00004* (2013.01); *A61B 2017/0406* (2013.01); *A61B 2017/0409* (2013.01); *A61B 2017/0414* (2013.01); *A61B 2017/0445* (2013.01); *A61B 2017/0446* (2013.01); *A61B 2017/045* (2013.01); *A61B 2017/0453* (2013.01); *A61B 2017/0458* (2013.01); *A61B 2017/0459* (2013.01); *A61B 2017/0475* (2013.01);
(Continued)

(58) Field of Classification Search
CPC ........ A61B 17/0401; A61B 2017/0409; A61B 2017/0414; A61B 2017/0445; A61B 2017/0458; A61B 2017/0459; A61B 2017/0496; A61F 2/0811; A61F 2002/0852
See application file for complete search history.

(56) References Cited

U.S. PATENT DOCUMENTS 6,511,498 B1 * 1/2003 Fumex ............... A61B 17/0401
606/232
7,229,441 B2 6/2007 Trieu et al.
(Continued)

*Primary Examiner* — Phong Son H Dang
(74) *Attorney, Agent, or Firm* — Norman F. Hainer, Jr.; Kate Ryland Tetzlaff

(57) ABSTRACT

Tissue repair systems which use knotless all-suture anchors and have the ability to lock multiple repair sutures within the anchor construct. The anchor construct includes a tension suture wrapped or looped upon itself to create an open eyelet, through which multiple repair sutures originating in soft tissue are passed. The location of the eyelet may be anywhere inside the all-suture anchor or adjacent to the exterior of the anchor body. Tensioning of the tension suture causes the eyelet to restrict movement of the repair sutures and secures them within or against the anchor body.

20 Claims, 9 Drawing Sheets

Related U.S. Application Data

(60) Provisional application No. 62/456,188, filed on Feb. 8, 2017, provisional application No. 62/417,058, filed on Nov. 3, 2016.

(52) U.S. Cl.
CPC ............... *A61B 2017/0496* (2013.01); *A61F 2002/0835* (2013.01); *A61F 2002/0852* (2013.01); *A61F 2002/0888* (2013.01); *A61F 2210/0004* (2013.01)

(56) References Cited

U.S. PATENT DOCUMENTS

| | | | |
|---|---|---|---|
| 9,962,149 B2* | 5/2018 | Brown | A61B 17/0401 |
| 9,962,150 B2* | 5/2018 | Rodriguez | A61B 17/06166 |
| 10,004,489 B2 | 6/2018 | Kaiser et al. | |
| 10,004,495 B2 | 6/2018 | Dimatteo et al. | |
| 10,058,319 B2 | 8/2018 | Konrath et al. | |
| 10,098,629 B2 | 10/2018 | Kaiser et al. | |
| 10,136,884 B2 | 11/2018 | Graul et al. | |
| 10,154,837 B2 | 12/2018 | Stone et al. | |
| 10,251,637 B2 | 4/2019 | Stone et al. | |
| 10,271,833 B2 | 4/2019 | Sengun | |
| 10,292,694 B2 | 5/2019 | Graul et al. | |
| 10,363,025 B2 | 7/2019 | Lantz et al. | |
| 10,492,776 B2 | 12/2019 | Dreyfuss et al. | |
| 10,542,967 B2 | 1/2020 | Kaiser et al. | |
| 10,595,845 B2 | 3/2020 | Burkhart et al. | |
| 10,595,851 B2 | 3/2020 | Kiser et al. | |
| 10,695,046 B2 | 6/2020 | Sugimoto et al. | |
| 10,973,622 B2 | 4/2021 | Mackay | |
| 11,116,498 B2 | 9/2021 | Martin | |
| 11,141,149 B2 | 10/2021 | Dimatteo et al. | |
| 11,219,446 B2 | 1/2022 | Bonutti et al. | |
| 11,272,915 B2 | 3/2022 | Sengun | |
| 11,311,287 B2 | 4/2022 | Stone et al. | |
| 11,331,094 B2 | 5/2022 | Graul et al. | |
| 11,457,958 B2 | 10/2022 | Bonutti | |
| 11,464,505 B2 | 10/2022 | Burkhart et al. | |
| 11,471,147 B2 | 10/2022 | Kaiser et al. | |
| 11,471,266 B2 | 10/2022 | Mackay | |
| 11,517,300 B2 | 12/2022 | Lantz et al. | |
| 2012/0150223 A1* | 6/2012 | Manos | A61B 17/0401 606/232 |
| 2012/0197271 A1* | 8/2012 | Astorino | A61B 17/0487 606/232 |
| 2012/0239085 A1* | 9/2012 | Schlotterback | A61B 17/0401 606/228 |
| 2013/0110165 A1* | 5/2013 | Burkhart | A61B 17/0401 606/232 |
| 2014/0277133 A1* | 9/2014 | Foerster | A61B 17/0401 606/232 |
| 2015/0351739 A1 | 12/2015 | Napolitano | |
| 2019/0117212 A1* | 4/2019 | Foerster | A61B 17/0401 |
| 2020/0205799 A1 | 7/2020 | Burkhart et al. | |
| 2020/0330088 A1 | 10/2020 | Sugimoto et al. | |
| 2021/0137672 A1 | 5/2021 | Mackay | |
| 2021/0244401 A1 | 8/2021 | Burkhart et al. | |
| 2022/0008069 A1 | 1/2022 | Martin | |
| 2022/0015757 A1 | 1/2022 | Stone et al. | |
| 2024/0057991 A1* | 2/2024 | Rodriguez | A61B 17/06166 |

* cited by examiner

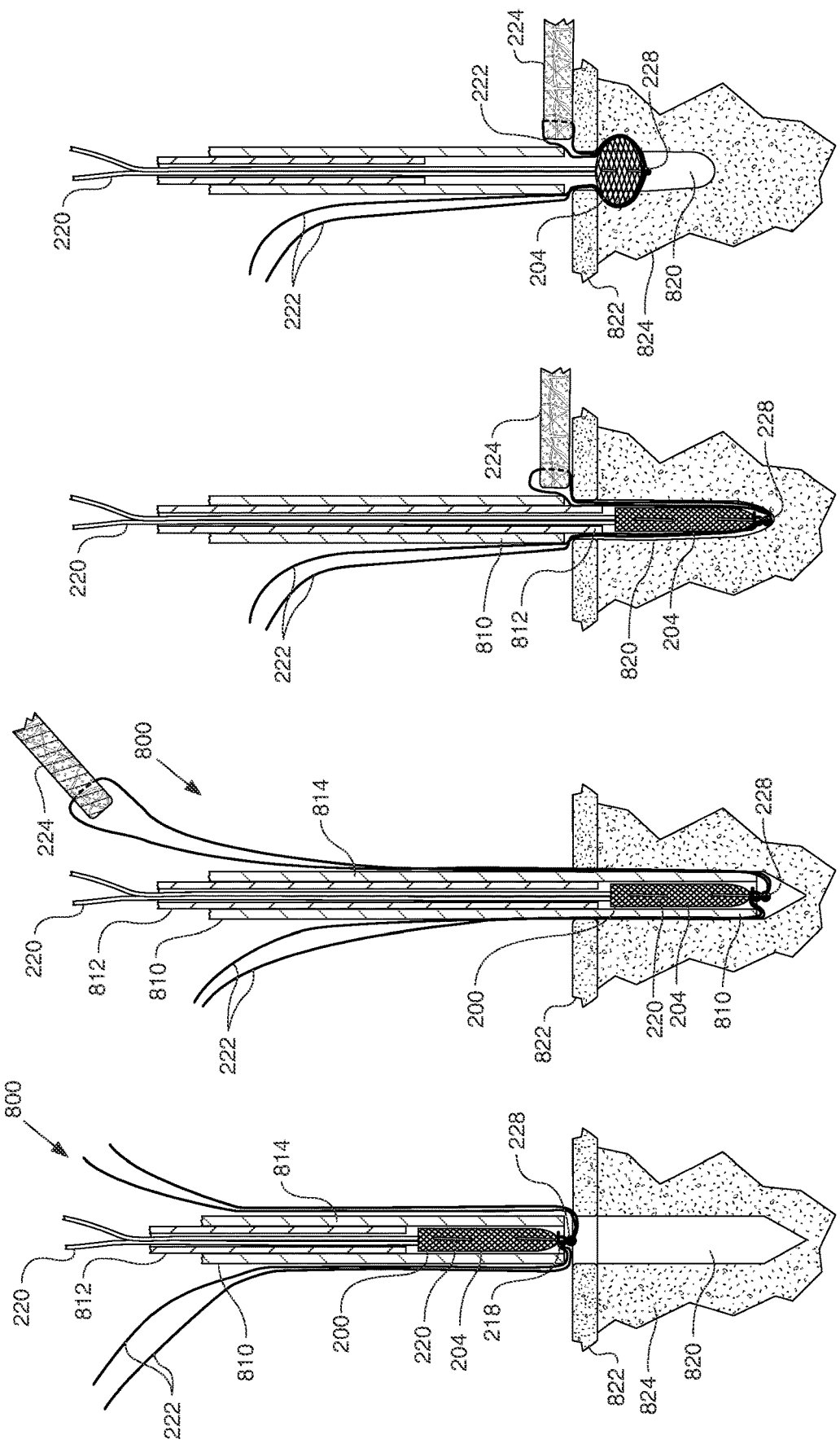

TISSUE REPAIR ASSEMBLY AND SYSTEM WITH SOFT ANCHORING IMPLANT

CROSS-REFERENCE TO RELATED APPLICATIONS

This application is a continuation of U.S. application Ser. No. 16/342,877 filed Apr. 17, 2019, which is a 371 application of PCT application No. PCT/US2017/059943 filed Nov. 3, 2017, which claims the benefit of U.S. Provisional Application No. 62/456,188 filed Feb. 8, 2017 entitled "Tissue Repair System with Soft Anchoring Implant" and U.S. Provisional Application No. 62/417,058 filed Nov. 3, 2016 entitled "Knotless Soft Anchor" the entirety of which are incorporated herein by reference in its entirety.

BACKGROUND

Many orthopedic surgeries involve the use of anchoring devices in procedures for attaching soft tissue to bone. Such procedures include attaching tendons to bone, bone to bone, tendons to tendons, and ligaments to bone, as well as ligament reconstruction. Most of these procedures rely on the use of polymeric, metal, or biodegradable rigid anchors with suture attached. The suture is passed through the tissue and a knot secures the construct together. However, the use of these anchors often requires rigid, hard materials to be placed in bone. If the anchors ever loosen, a surgeon or surgical technician is faced with the problem of having a potentially hard device migrate into a patient's joint, placing the patient at risk for arthritis. Additionally, certain polymers, such as polylactic acid (PLA), can weaken bone, predisposing a patient's bone to fracture. Furthermore, the knot used to secure the tissue is often located external to the bone and may generate discomfort for the patient. Accordingly, an anchor that uses only soft, flexible materials enables less-invasive techniques for implantation because the material is less brittle. Securing the repair sutures within the bone may additionally relieve patient discomfort seen with external knots. Moreover, the use of soft anchors poses no risk of lodging in a joint or body cavity, and leads to stronger bone and lower risk of fracture.

Current examples of soft anchors include anchors made entirely of flexible suture material. These all-suture anchors are created by assembling a braid within itself or inside a second similar construct. Tension on the inside braid approximates soft tissue to bone or tissue to tissue, while tension on the outside braid locks the inside and outside braids together. Thus, the braided all-suture construct behaves like a "Chinese finger lock"—that is, friction between the opposing braid fibers provides resistance to motion. However, these constructs have a significant number of procedural steps for deployment and are limited to use with a single repair suture rather than multiple sutures. Additionally, many all-suture anchors must be manually deployed by the surgeon or surgical technician. Thus, the ability to tension sutures is limited by the skill of the person applying the tension.

BRIEF SUMMARY

Described herein are tissue repair systems which use a knotless all-suture anchor construct. The tissue repair systems of this disclosure maximize the locking force in fixation of soft tissue to bone, and have the ability to constrict or lock repair sutures within the anchor construct. The sutures may number a single strand or any multiple of sutures strands. For example, the tissue repair systems of this disclosure could be used to fixate a single suture passed through labral tissue or could be used to laterally fixate multiple repair sutures originating from a medial row during a rotator cuff repair.

The anchor construct of the tissue repair systems includes a tension suture wrapped or looped upon itself to create an open eyelet, through which one or more repair sutures originating from soft tissue are passed. The location of the eyelet may be anywhere inside the all-suture anchor or adjacent to the exterior of the anchor body. Multiple wraps or loops of the tension suture may be utilized to form multiple eyelets. Tensioning of the tension suture causes the at least one eyelet to form a tortuous path around the repair suture and constrict them within or against the anchor body. Alternately, the wrapped or looped tension suture may include at least one eyelet that form a knot construct. A specialized delivery system provides nearly twice the force to the tension suture than a force provided by a human hand. Thus, use of the tissue repair systems of this disclosure generates a greater locking force than the friction lock or pre-tied knots of prior art devices, and may require fewer steps for deployment.

Further examples of the tissue repair system of this disclosure may include one or more of the following, in any suitable combination.

In examples, the tissue repair system of this disclosure includes a tubular, soft anchor body having a proximal end, a distal end, and a longitudinal axis extending therebetween. A suture is coupled to the anchor body such that first and second ends of the suture exit the anchor body adjacent to the proximal end of the anchor body. The tissue repair system also includes at least one eyelet formed by the suture. The at least one eyelet defines at least one opening for the passage of at least one flexible member. Tensioning of the first and second ends of the suture causes the anchor body to change from a first configuration, in which the anchor body is elongate, to a second configuration, in which the anchor body is axially compressed and radially extended. Tensioning of the first and second ends of the suture also causes the at least one eyelet of the suture to secure the at least one flexible member to the anchor body.

In further examples of the tissue repair system, at least one of the proximal end and the distal end of the anchor body is open. In examples, the at least one eyelet is in the form of a knot, which may be in the form of a luggage tag. The luggage tag may be twisted to form a figure eight or doubled to form a Prusik knot or other form of locking knot. In other examples, the at least one eyelet is in the form of a wrap, winding, or spiral. The tissue repair system may further include a tubular member extending through a length of the wrap, winding, or spiral for passage of a suture passer. The at least one eyelet can be formed external to the anchor body or internal to the anchor body. The at least one eyelet can also be formed adjacent to the distal end of the anchor body, or proximal to the distal end of the anchor body.

In yet further examples of the tissue repair system, the suture extends along a first side wall of the anchor body from the proximal end to the distal end, crosses the distal end, and returns along a second side wall opposite the first sidewall from the distal end to the proximal end. In other examples, the suture extends along an internal volume of the anchor body from the proximal end to the distal end, returns along a first side wall of the anchor body from the distal end to the proximal end, crosses the proximal end, returns along a second side wall opposite the first sidewall from the proximal end to the distal end, and extends along the internal volume from the distal end to the proximal end. In further examples, the suture is coupled to the anchor body in an "S" shaped configuration or in a "C" shaped configuration.

Examples of a method of tissue repair of this disclosure include: 1) passing at least one flexible member through the at least one opening in the at least one eyelet; 2) inserting a soft anchor body of this disclosure as described above into a bone hole; and 3) tensioning the first and second ends of the suture. Tensioning the first and second ends of the suture causes the anchor body to change from a first configuration, in which the anchor body is elongate, to a second configuration, in which the anchor body is axially compressed and radially extended. Tensioning the first and second ends of the suture also causes the at least one eyelet of the suture to secure the at least one flexible member to the anchor body. In the second configuration, the anchor body becomes lodged within the bone hole.

Further examples of the method of this disclosure include forming the bone hole in bone. In examples, passing the at least one flexible member through the at least one opening in the at least one eyelet includes passing the at least one flexible member with a suture passer or snare. In other examples, passing the at least one flexible member through the at least one opening in the at least one eyelet includes passing the at least one flexible member through a tubular member associated with the suture passer. In examples, tensioning the first and second ends of the suture includes tensioning the first and second ends of the suture by hand. In other examples, tensioning the first and second ends of the suture includes tensioning the first and second ends of the suture with a specialized delivery device.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 8A-8D illustrate examples of tissue repair systems;

DETAILED DESCRIPTION

Figure 1A:
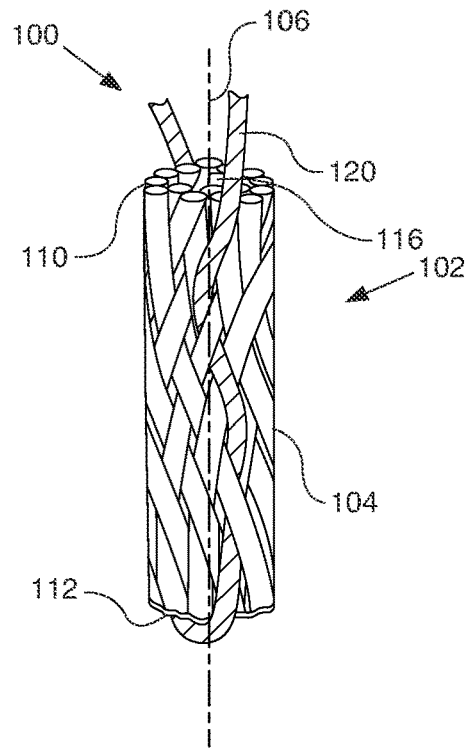
FIGS. 1A-1C illustrate a prior art tissue repair system using a soft anchoring implant.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

Comprise, include, and/or plural forms of each are open ended and include the listed parts and can include additional parts that are not listed. And/or is open ended and includes one or more of the listed parts and combinations of the listed parts.

Referring now to FIG. 1A, an exemplary tissue repair assembly 100 known in the art is shown. Generally described, tissue repair assembly 100 comprises a soft anchoring implant 102 and a tension suture 120. The implant 102 has a three-dimensional, tubular shaped body 104 extending along a longitudinal axis 106. The implant body 104 includes a proximal end 110, which may be open and in communication with an internal or resident volume 116, and a distal end 112, which may be open or closed. In the example of FIG. 1A, the suture 120 passes through the wall of the implant body 104 to the outside for a short distance before it passes back between fibers of the implant body 104 to the inside of the implant body 104, and possibly into the internal volume 116, then out again by passing between the fibers or braids and around the distal end 112 of the implant body 104 before repeating the penetrations and exiting back out around the proximal end 110 of the implant body 104. In other examples, not shown, the suture 120 may extend along the interior or the exterior of the implant body 104 without penetrating the walls of the implant body 104. Notably, the suture 120 is not locked into place with respect to the implant body 104, but rather remains slideable through or along the walls of the implant body 104.

Figure 1B:
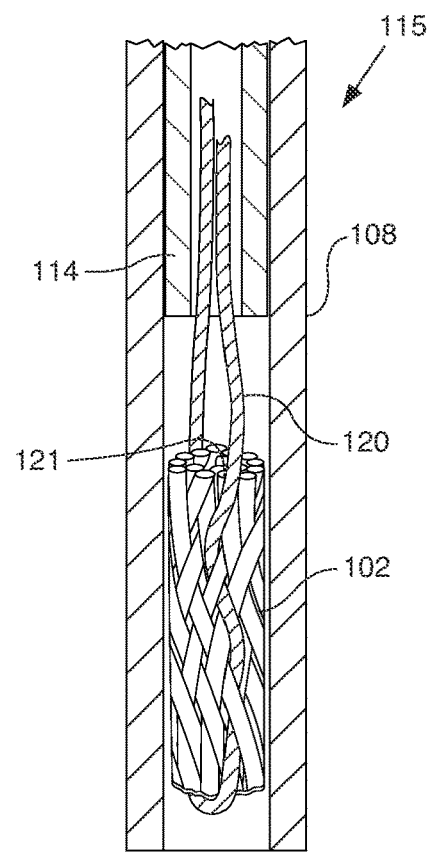

As shown in FIG. 1B, the implant 102 is intended to anchor the suture 120 within bone or other hard tissue (not shown here) and allow for the further attachment of soft tissue to the suture 120. Preferably, the implant 102 is loaded into a dedicated delivery system 115, including an inserter tube 108 and implant pusher 114 and deployed into the hard tissue to facilitate a repair. Non-limiting examples of such specialized delivery systems 115 are generally described in U.S. Publication No. 2013/0123810 (Brown et al.), incorporated by reference herein. In other examples, not shown, the implant 102 may be deployed as a retaining anchor for two pieces of soft tissue.

Examples of the implant 102 may be formed from a soft, flexible construct of braided yarns or fibers that has been rolled into a tube or cone shape. Typical materials that would be used to construct the implant 102 may be, but are not restricted to, ultra-high molecular weight polyethylene (UHMP), polyester, polypropylene, silk or bio absorbable materials typically used for suturing applications. The rolled structure may be held together with adhesive or stitches and the free edge of the braided material may be bound further in similar methods. Other non-limiting examples of soft anchoring implants 102 include the Q-Fix all-suture implant, manufactured by ArthroCare Corporation, Tex., USA, and generally described in U.S. Publication No. 2013/0123810 (Brown et al.), incorporated by reference herein. As shown in FIGS. 1A-1B, in the pre-deployed state, the fibers of the implant body 104 are relaxed in an orientation neither substantially parallel with the longitudinal axis 106 nor orthogonal to the longitudinal axis 106 of the implant body 104.

Figure 1C:
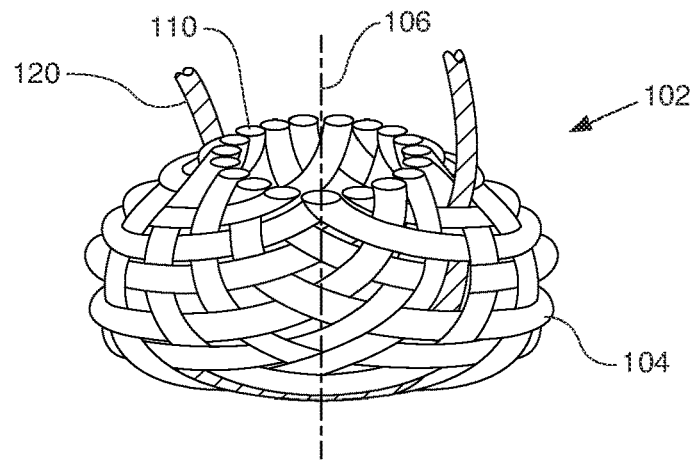

Turning now to FIG. 1C, when the suture 120 is tensioned and some counter traction is applied at the proximal end 110 of the implant body 104; the implant body 104 shortens along its longitudinal axis 106 and, in doing so, expands radially. This radial expansion forces the implant body 104 to assume a larger effective diameter than it had prior to deployment and larger than the hole into which it was inserted. In the deployed state, the fibers of the implant body 104 are more aligned in an orientation parallel to the longitudinal axis 106 and are generally more compacted. Thus, the anchoring aspect of the implant 102 is achieved.

Generally, the soft anchoring implant 102 is in the form of a three dimensional structure either like that of a sock with a closed end tube or an open ended tube. This three-dimensional structure preferably defines or includes a pre-defined inner space or resident volume 116. The "resident volume" is a volume that is intentionally formed by the three-dimensional anchoring implant structure in its manufactured, predeployed or relaxed state. A resident volume as defined herein may be inherently thicker and/or wider than the thickness of the material from which the structure is fabricated. For example, a flat piece of braided material with a hole in it may not define a resident volume (the hole), because the hole is only as deep as the thickness of the braided material. It is not necessarily a permanently open or enclosed volume. For example, as in the case of soft flexible braided materials, said resident volume 116 may exist upon manufacture and inherently in the structure, but when the sides of the structure are compressed, the resident volume 116 may become smaller or disappear altogether. The resident volume 116 may exist as manufactured in the structure of the anchoring implant body 104 when the implant resides in an upright configuration but tend to disappear when the structure is on its side due to the forces of gravity on the soft, flexible braided material of the structure. However, the resident volume 116 always exists within the structure when the structure is returned to its original position and configuration. The term as it is used herein does not necessarily preclude the resident volume 116 from being filled with some other substance at a given time nor does it preclude the structure folding or collapsing in on itself so as to temporarily obscure the presence of the resident volume. The biaxial braided material of the soft anchoring implant can be configured to define a resident volume when in a relaxed state, a substantially reduced resident volume when loaded into an insertion device, and substantially no resident volume when fully deployed to tissue. Further discussion of the resident volume is generally described in U.S. Publication No. 2013/0123810 (Brown et al.), incorporated by reference herein.

Figure 2A:
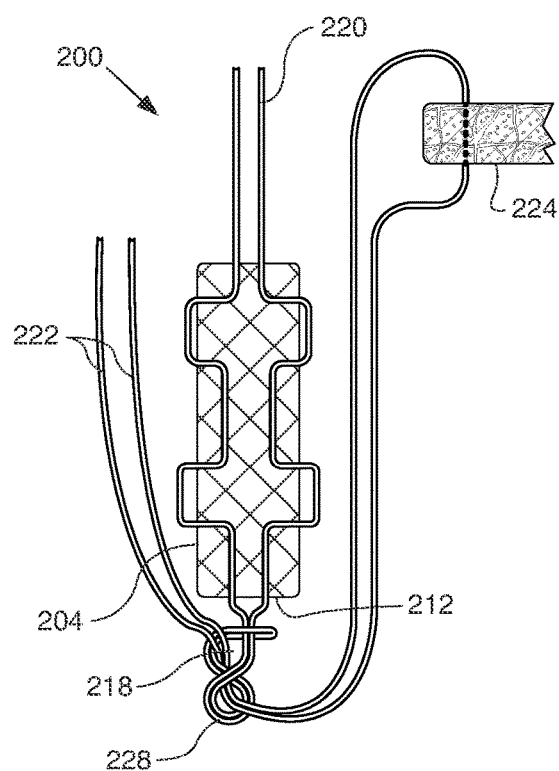
FIGS. 2A-2B illustrate a first example of a tissue repair assembly of this disclosure with distal, external eyelets.
Figure 2B:
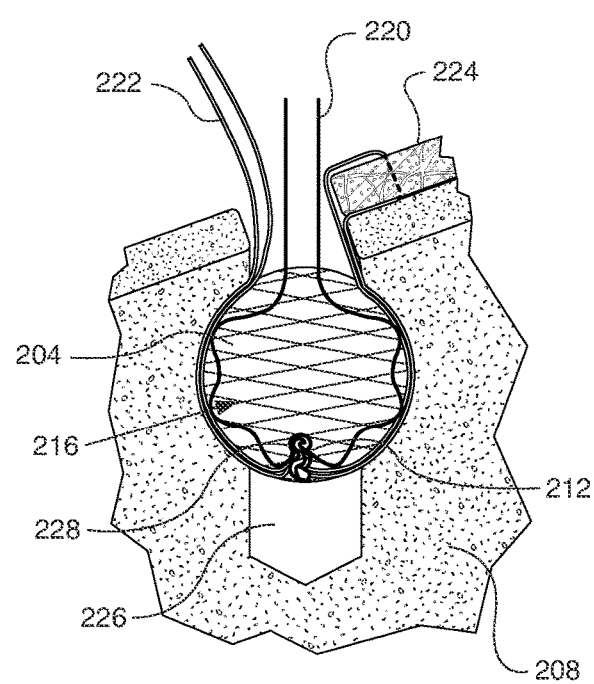

The discussion will now turn to FIGS. 2A-2B, illustrating a first example of a tissue repair assembly 200 of this disclosure. The tissue repair assembly 200 is similar to the tissue repair assembly 100 of FIGS. 1A-1C, except as described below. In the tissue repair assembly 200, a tension suture 220 is coupled to the implant body 204 in a similar manner to how the suture is interwoven with implant body 104 in FIGS. 1A-1C, except that the tension suture 220 is wrapped or looped upon itself to form at least one eyelet 218 adjacent to the distal end 212 of the implant body 204. For example, multiple eyelets 218 may be configured into a loosely formed knot 228 formed by a portion of the tension suture 220. The knot 228 can be any type of hitch, bend or locking knot known in the art, examples of which are further described below. One or more repair sutures 222 (two, as shown) originating from soft tissue 224, are threaded or passed through the eyelet 218 or knot 228, as further described below. Tension may be maintained on the repair sutures 222 while the implant body 204 is inserted into a pre-formed bone hole 226, as shown in FIG. 2B. With the soft tissue 224 approximated to the bone hole 226, the implant body 204 is partially or fully deployed as described above with regard to tissue repair assembly 100. A partial deployment may be defined as a configuration wherein the anchor body 204 may be partially radially expanded while the eyelet 218 is in a configuration such that repair sutures 222 are slideable through the eyelet 218 so as to adjust the approximation of soft tissue 224 to the bone hole 226; additional approximation achieved by additional tension applied to free ends of the repair sutures 222. In a fully deployed configuration, the soft anchor body 204 is fully deployed so as to be more radially expanded and axially shortened than a partially deployed configuration, so as to significantly reduce or eliminate the resident volume 216 of the anchor body 204 and engage a length of the bone hole 226. In a fully deployed configuration the at least one eyelet 218 is in a configuration that prevents repair suture 222 sliding through the eyelet. This configuration may include a reduced loop or eyelet size, or may alternatively or in addition to, form a tortuous path for the repair suture 222 sufficient to resist sliding. Generally the at least one eyelet 218 is altered so as to bind with or lock with the repair suture 222, so as to prevent repair suture 222 from sliding through the eyelet. Supplemental securement of the repair suture 222 may also be provided between the length of repair suture 222 that extends along the length of the anchor body 204 and between the anchor body 204 and bone hole, as the anchor body radially expands and compresses the length of repair suture against a portion of the bone wall.

Depending on whether the distal end 212 of the implant body 204 is open or closed, the eyelet 218 or knot 228 may be drawn inside the implant 204 or drawn against the distal end 212 of the implant 202 respectively upon deployment. Under tension, the tension suture 220 unwraps or unwinds the eyelet 218 to an extent that a tortuous path and friction constrict movement of the repair sutures 222. Alternately, the tension suture 220 constricts around the repair sutures 222 to an extent that the eyelet 218 or knot 228 locks the repair sutures 222. Thus, the action of deploying the implant 204 both locks the implant body 204 into bone 208 and also secures the repair sutures 222 to the anchor body 204, effectively fixing the repair sutures 222 and thereby the soft tissue 224 to bone 208.

Figure 2C:
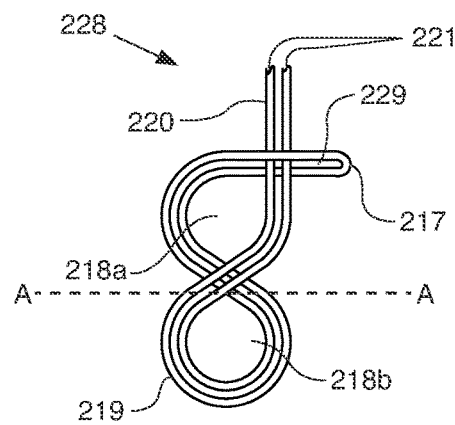
FIGS. 2C-2H show examples of the eyelets of FIGS. 2A-2B.
Figure 2D:
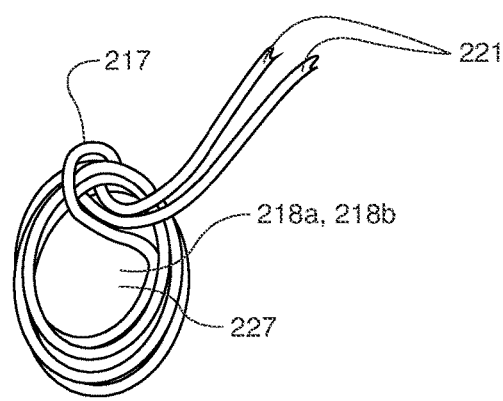
Figure 2E:
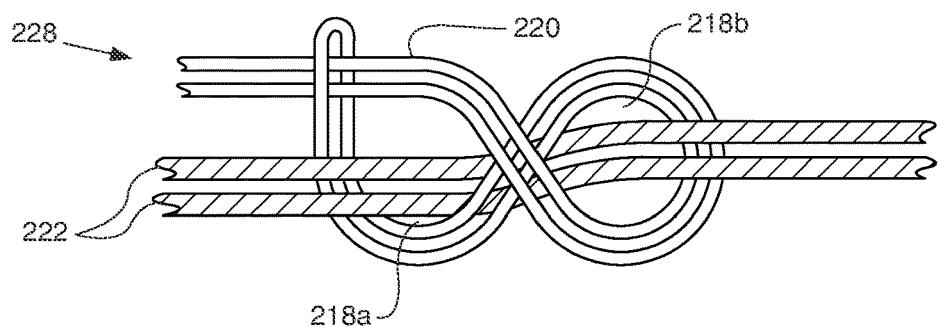
Figure 2F:
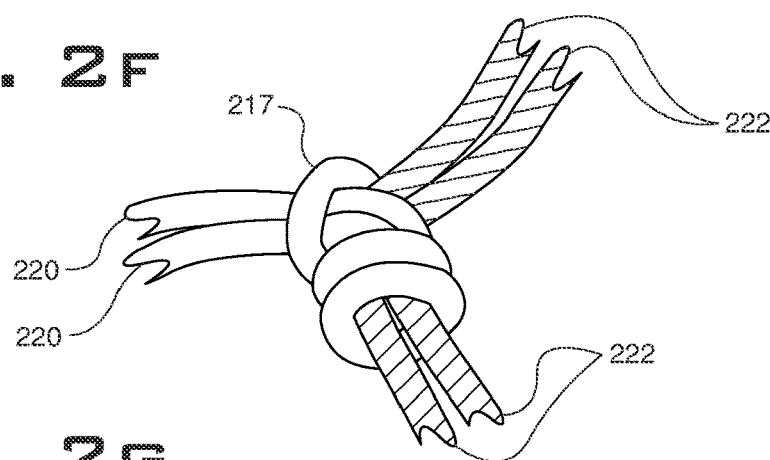

FIGS. 2C-2F are detailed illustrations of an example of the knot 228 described above with regard to FIGS. 2A-2B. In FIG. 2C, the tension suture 220 forms a figure eight shape having a primary loop 217 and a secondary loop 219, with the ends 221 of the tension suture 220 passing through a gap 229 formed by the primary loop 217. Tension suture 220 may be a different material and size to repair suture 222. For example tension suture 220 may comprise a typical material not restricted to, ultra-high molecular weight polyethylene (UHMP), polyester, polypropylene, silk or bio absorbable materials typically used for suturing applications and may be a flexible member including a structure similar to suture or tape. Repair suture 222 may be a flexible member also in a suture or tape, including typical materials such as those listed above. Repair suture 222 may include a different material or size than tension sutures 220, so that repair 222 may more easily slide through knot 228 for example. The primary loop 217 and the ends 221 of the tension suture 220 define a first eyelet 218a while the secondary loop 219 defines a second eyelet 218b. 2D shows a knot configuration formed by folding the second eyelet 218b along line A-A shown in FIG. 2C so that the first and second eyelets 218a, 218b together form a conjoined eyelet 227 of the knot 228. In FIG. 2E, it can be seen that each of the repair sutures 222 may pass through both eyelets 218a, 218b in the knot 228. As shown in FIG. 2F, with counter-tension held on the repair sutures 222, the tension suture 220 is pulled in a substantially opposite direction to form the knot 228. Optionally, one or more of the repair sutures 222 can be pulled to test the retention force of the knot 228.

Figure 2G:
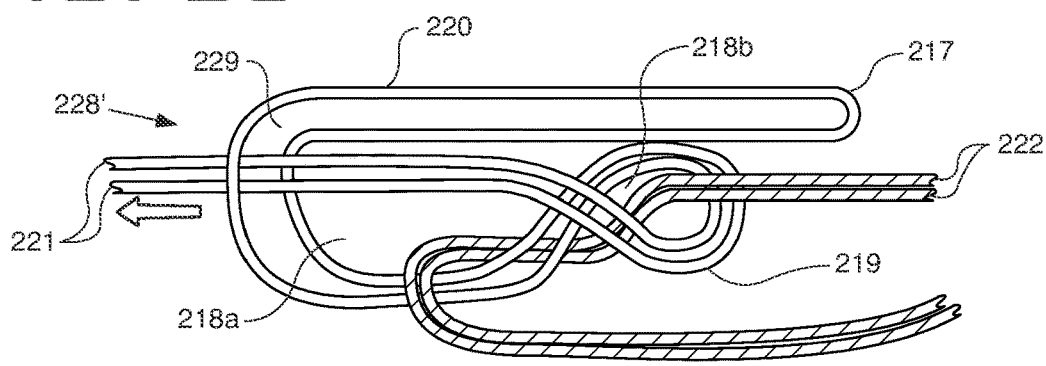
Figure 2H:
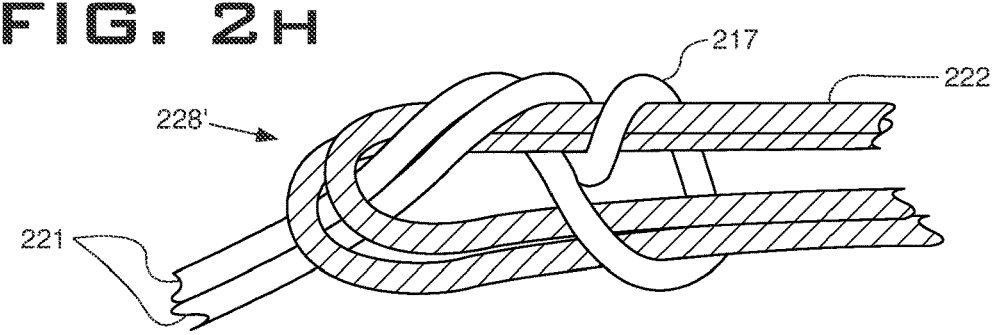
Figure 2I:
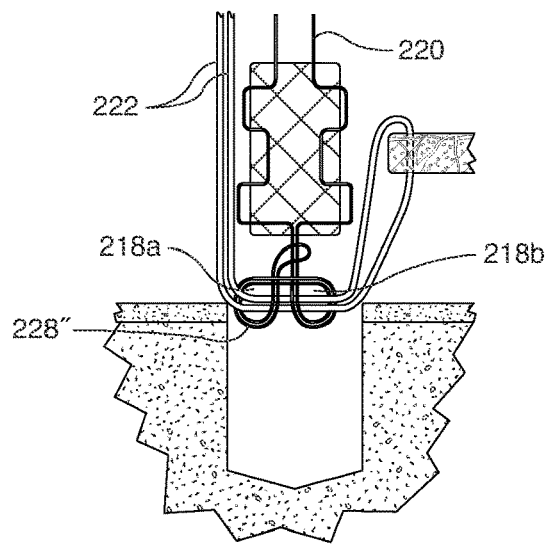
FIG. 2I illustrates a further example of a tissue repair assembly of this disclosure with distal, external eyelets.

Another example of forming the knot 228 is shown with regard to FIGS. 2G-2H. In FIG. 2G, the tension suture 220 is configured in the same way as described above with regard to FIGS. 2C-2F. However, in use, the primary loop 217 is maintained distal of the secondary loop 219 until the secondary loop 219 is tensioned. With a distal counter-tension held on the repair sutures 222 the tension suture 220 is pulled in a proximal direction (arrow indicated) to form the knot 228'. Tensioning the knot 228' also moves the secondary loop 219 proximal through the gap 229 in the primary loop 217 and permits the primary loop 217 to fold back over the repair sutures 222, as shown in FIG. 2H. With the primary loop 217 folded over the repair sutures 222, a stronger knot 228' is formed with the suture 220 as compared with the knot 228 of FIGS. 2A-2B. FIG. 2I shows an additional example of a knot 228", where the knot 228" is in the shape of a luggage tag. The luggage tag may be twisted to form a figure eight or doubled to form a prusik knot or other form of locking knot defining eyelets 218a, 218b through which the repair sutures 222 are passed.

Figure 3:
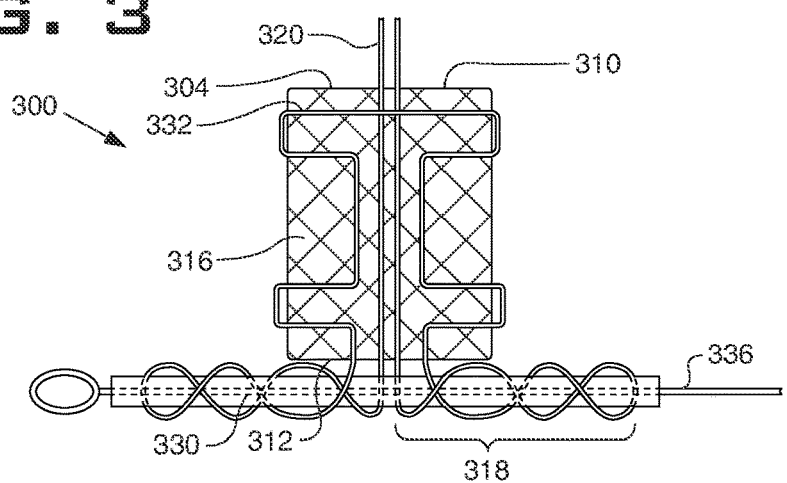
FIG. 3 illustrates another example of a tissue repair assembly with distal, external eyelets in the form of a spiral, wrap, or winding.

Another example of a tissue repair assembly 300 of this disclosure is shown in FIG. 3. The tissue repair assembly 300 is similar to the tissue repair assembly 100 and 200, except that the tension suture 320 extends through the internal volume 316 of the implant body 304 from the proximal end 310 to the distal end 312. The tension suture 320 then forms at least one eyelet 318 by spiraling around a first section of an optional suture passer 336 for retrieving the repair sutures adjacent to the distal end 312 of the implant body 304. Alternatively, the eyelets 318 spiral around a first section of a loading tube 330 associated with the suture passer 336. The tension suture 320 may then return along and may weave through a wall of the implant body 304 from the distal end 312 to the proximal end 310 and cross the implant body 304 at a suture cross 332 near the proximal end 310 of the implant body 304. The tension suture 320 then extends along and may extend through an opposite wall of the implant body 340 from the proximal end 310 to the distal end 312 to spiral around a second section of the optional suture passer 336 (and loading tube 330). The suture 320 may then return through the internal volume 316 of the implant body 304 from the distal end 312 to the proximal end 310. This configuration forms the deployment mechanism and constriction mechanism around the repair sutures 322 (not shown) to the implant body 304, as described above with regard to the tissue repair assembly 200.

Figure 4:
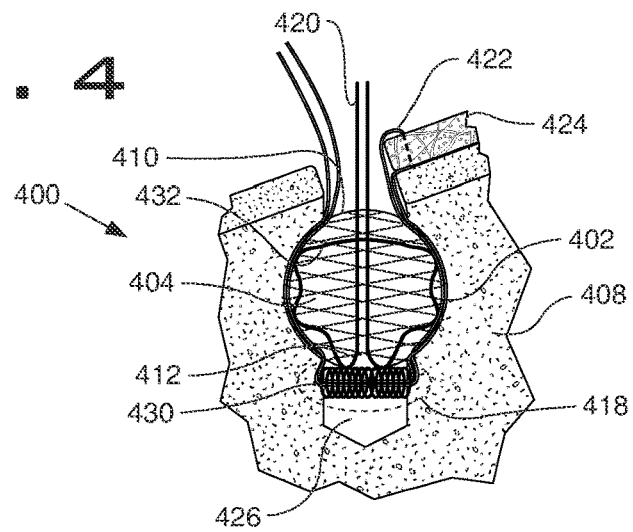
FIG. 4 shows a tissue repair assembly of this disclosure deployed in bone.

An example of a tissue repair assembly 400 of this disclosure is shown in FIG. 4. The tissue repair assembly 400 is similar to the tissue repair assembly 300 described above except that one or more repair sutures 422 originating from soft tissue 424 are constricted or locked by eyelets 418 formed by a plurality of wraps or windings 430 of the tension suture 420 at or near the distal end 412 of the implant body 404. After placement of the implant 402 and the repair sutures 422 into a bone hole 426, the repair sutures 422 are tensioned to approximate the soft tissue 424 to bone 408. Deployment (or partial deployment) of the implant 402 draws the suture cross 432 at the proximal end 410 of the implant body 404 towards the distal end 412 while also locking the repair sutures 422 at the distal end 412 via the wraps or windings 430. The significant tension applied by the tension suture 420 and the implant 402 locks the implant body 404 and the repair sutures 422 into bone 408.

Figure 5A:
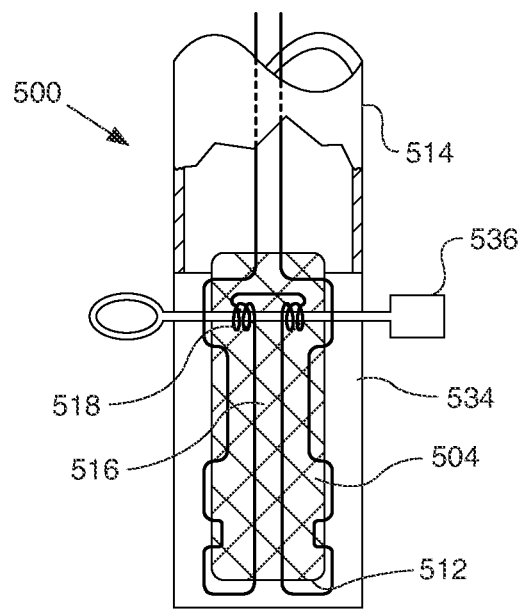
FIGS. 5A-5B illustrate a further example of a tissue repair assembly and system with proximal, internal eyelets.
Figure 5B:
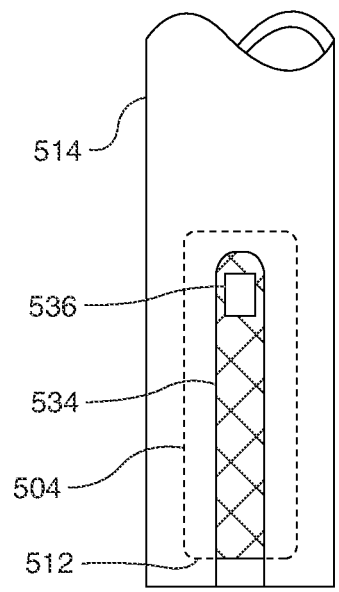
Figure 5C:
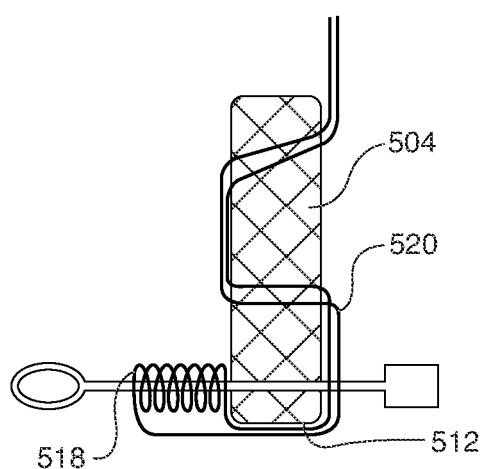
FIGS. 5C-5D illustrate yet further examples of tissue repair assembly with external eyelets.
Figure 5D:
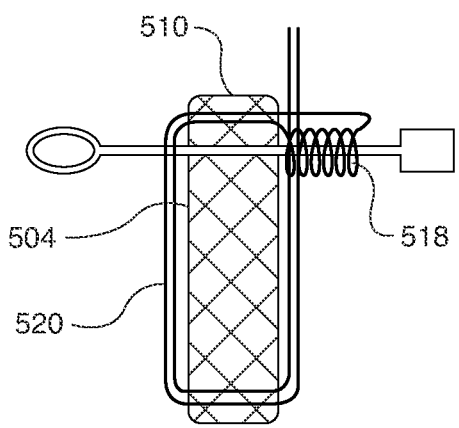

Yet further examples of a tissue repair system 500 including a tissue repair assembly and delivery device are shown in FIGS. 5A-5D. In FIG. 5A a front view of a delivery device is shown, with a portion of outer tube 514 removed and FIG. 5B is a side view relative to FIG. 5A, including the outer tube 514, the tissue repair assembly shown in system 500 is similar to the tissue repair assembly 300 and 400 except that the eyelet 518 is located in alternative locations such as within the internal volume 516 of the implant body 504 or to the side of the implant body 504. System 500 shows an outer tube of a delivery device 514, the outer tube 514 having elongate slots 534 extending up to and including a terminal edge of the outer tube 514 to permit the repair sutures (not shown) to be pulled by a suture passer 536 directly through the implant body 504. The repair sutures are thus located adjacent a proximal portion of the implant body 504. FIG. 5C shows an alternative example in which at least one eyelet 518 is located external to the implant body 504, and proximal to the distal end 512 on a first lateral side of implant body 504. In addition, the tension suture 520 is shown with an alternate weaving configuration, being woven through the implant body 504 in an "S" shaped configuration, extending along a first lateral side of the implant 504, through the thickness of the implant body 504 to a and along a second lateral side, at least once as the tension suture 520 extends along the implant body 504. FIG. 5D shows yet another alternative example in which the eyelet 518 is located external to the implant body 504 near the proximal end 510, the tension suture 520 being woven through the implant body 504 in a "C" shaped configuration. A slot or aperture through the delivery device 514 to permit repair sutures to be pulled by a suture passer 536 and then be removed from the outer tube 514 may be required similar to that required in FIGS. 5A and 5B. Thus, in the examples of the tissue repair system 500 described above, the locking mechanism formed by the tension suture 520 is spaced proximally from a distal terminus of implant body 504 either internal (FIGS. 5A-5B) or external (FIGS. 5C-5D) to the implant body 504.

Figure 6A:
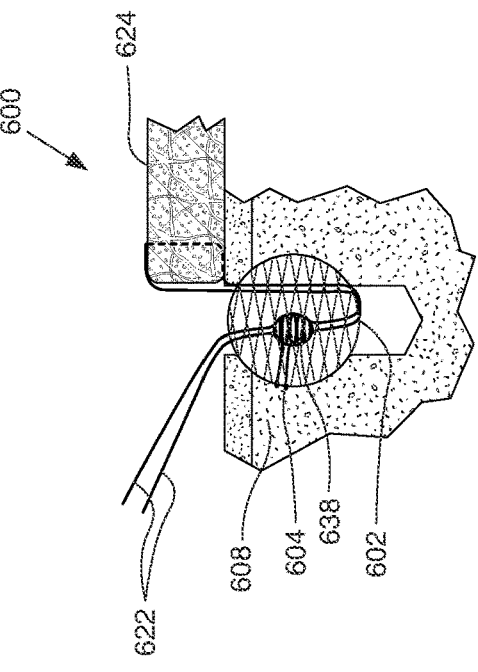
FIGS. 6A-6B and 7A-7C illustrate alternative examples of tissue repair assemblies for use with a pre-tied knot.
Figure 6B:
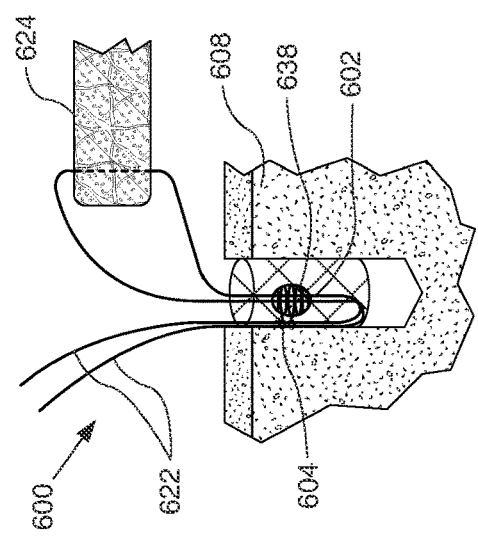

The tissue repair assemblies 200, 300, 400 and system 500 described above relate to knotless soft anchors. As discussed above, knotless systems have the advantage of not leaving a pre-tied knot visible and tactile external to the bone hole. Alternative examples of tissue repair assemblies of this disclosure could include soft and/or rigid anchor assemblies as illustrated in FIGS. 6A-6B and 7A-C. For example, in the tissue repair assembly 600 shown in FIGS. 6A-6B, a pre-tied knot 638, such as a prusik knot (or other friction mechanism) may be coupled to and disposed inside the soft anchor implant 602. Coupling 604 is shown as a tethered coupling to a portion of anchor sidewall, which may include a loop or portion of knot 638 that is interwoven with implant 604. Alternative coupling means may include an adhesive, or a separate distinct loop of suture. Repair suture 622 may extend through a portion of pre-tied knot 638 and a tension suture to deploy the anchoring implant 602 (not shown) may extend through anchoring implant 602, separate from or not directly coupled to pre-tied knot 638. Alternatively no tension suture may be required and repair suture 622 may be tensioned so as to deploy anchor 602, to a configuration shown in FIG. 6B. If this is the case, pulling on end of repair suture 622 may simultaneously deploy anchor 602 as shown in FIG. 6B, draw the soft tissue towards bone 608 and lock repair sutures 622 in place. The knot 638 may be a locking knot or one-way friction mechanism that may limit sliding of the repair suture 622 to a single direction through loops of knot 638 and therefore the repair suture 622 is locked via the inherent mechanism of the knot 638. Alternatively the tethered coupling 604 may tighten knot 638 as it is pulled radially outward during anchor deployment. Using a separate tensioning suture (not shown) threaded through the anchoring implant 602 may allow the tissue 624 to be at least partially drawn towards the bone 608 first before tensioning the tensioning sutures to deploy the anchoring implant 602. After full anchor deployment as shown in FIG. 6B repair suture ends 622 may be further drawn to finely tune position of soft tissue 624 and knot 638 may lock suture 622 as described above.

Figure 7A:
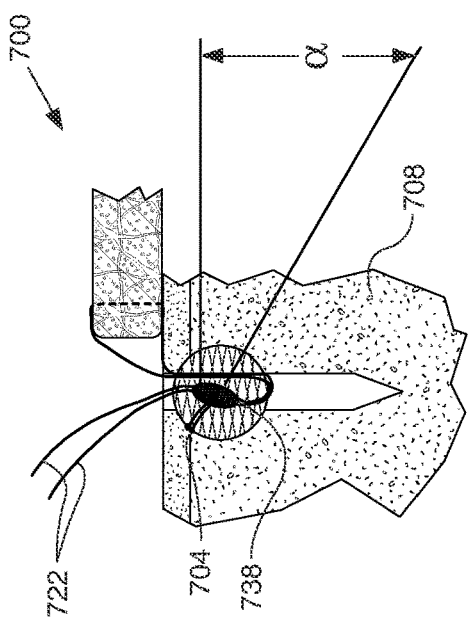
Figure 7B:
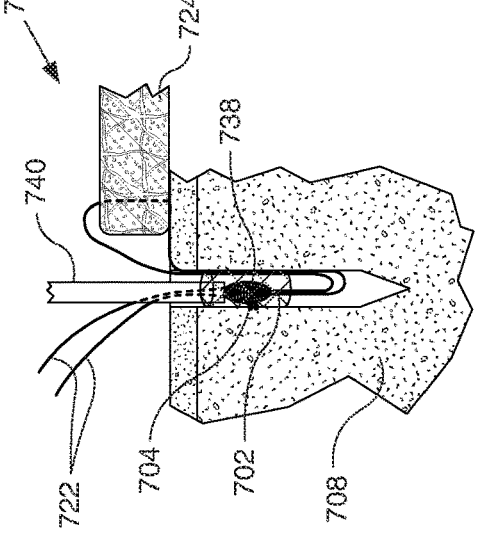
Figure 7C:
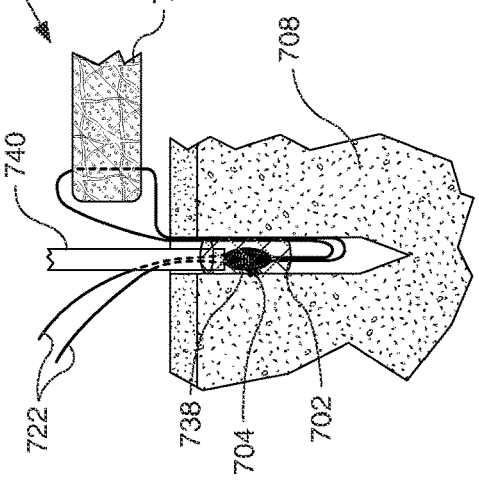

Another example of a tissue repair assembly 700 is shown in FIGS. 7A-7C. The tissue repair assembly 700 includes an implant 702, which may be either soft or rigid, plus a pre-tied knot 738 internal to the implant 702. Similar to assembly 600, the repair sutures 722 are snared through the pre-tied knot 738 internal to the implant 702. While in bone 708, a stabilizer rod 740 keeps the pre-tied knot 738 in an immobile position (FIG. 7A) and repair suture 722 may be snared through a bore or channel of stabilizer rod. Immobilizing the pre-tied knot 738 via the stabilizing rod 740 may allow the repair sutures 722 to be reduced smoothly (FIG. 7B) so as to move the soft tissue 724 to a desired location. The stabilizer rod 740 may be removed once the tissue 724 is in the desired location (FIG. 7C), at which point the repair sutures 722 may be locked in position by the knot mechanism as described above. In addition, since the soft tissue 724 is now in the desired location, the pre-tied knot 738 may have limited movement due to tension from the portion of repair suture 722 that extends through soft tissue 724 and around a distal end of anchoring implant 702, preventing or limiting the knot 738 movement in a proximal direction as the anchor is deployed. However similar to assembly 600, the pre-tied knot is coupled to the anchor. As the anchor deploys and shortens axially, at least partially opposing tensions may then be applied to the pre-tied knot 738 causing knot 738 to rotate; the opposing tensions being from the knot coupling 704 that may move in a proximal direction during deployment and tension on repair suture 722 extending through the soft tissue 724. This rotation may increase the lock strength between the pre-tied knot 738 and repair sutures 722.

Turning to FIG. 8A, a section view is shown of the tissue repair system 800, including an insertion tool distal end 810 and tissue repair assembly such as assembly 200, 300, 400 or 500 described in earlier figures. FIG. 8A shows the soft anchoring implant 204 loaded into the outer inserter tube 814. The inserter tube 814 is preferably metal and its diameter is generally the same as the diameter of a target bone hole 820 that is drilled or otherwise formed in the cortical bone 822 and cancellous bone 824 into which the implant is to be inserted. A length of tension suture 220 is shown woven through the implant 204 as described previously with the free ends of the tension suture exiting the end of the soft anchoring implant and subsequently exiting the inserter tube 814 and the coaxial implant pusher 812. Knot 218 is shown at distal end of implant 204, and adjacent distal opening of inserter tube 814. Knot 218 may be sheltered inside tube 814 or may be slightly exposed or coincident with the opening of the inserter tube 814 so as to be more accessible by a snare or suture passer (not shown). The implant pusher 812 is preferably but not necessarily a metal tithe with an outer diameter generally the same as (or slightly smaller than) the outer diameter of the soft anchoring implant 204 and slightly smaller than the inner diameter of the inserter tube 814.

A close but slideable fit between the outer diameter of the implant pusher 812 and the inner diameter of the inserter tube 814 aids in preventing portions of the soft anchoring implant 204 from becoming wedged between the two tubes and provides generally better counter traction. In practice, however, a close fit between the outer diameter of the implant pusher 812 and the inner diameter of the inserter tube 814 may be hard to achieve. The end of the implant pusher 812 may be configured to have a flare. Alternatively the end may be configured in any other manner, such as a bead, roll or additional component which will allow a closer fit to the inner diameter of the inserter tube or otherwise prevents pinching of the implant 204 between the inserter tube 814 and the implant pusher 812. The lumen of implant pusher 812 is of sufficient diameter as to allow the free passage of both ends of the tension suture 220.

When the tissue repair system is used in a bone anchoring scenario such as a rotator cuff repair or a labral repair, a hole 820 may be drilled into the bone where the soft anchoring implant assembly such as assembly 200 described earlier is to be placed. This may be done using a standard orthopedic drill to a predetermined depth. The depth of the hole 820 is typically about the same as or slightly longer than the length of the implant assembly 200. Before placing the assembly 200 into the prepared bone hole, a repair suture 222 may be coupled to soft tissue and then threaded through at least one of the eyelets 218. This may be achieved with a preassembled snare, suture passer (not shown) that extends through the at least one eyelet 218. An optional suture loader or tube (not shown) may also extend through the at least one eyelet so as to ease maintenance of the eyelet configuration while threading the repair suture 222.

As shown in FIG. 8B, the inserter tube 814 with soft anchoring implant assembly 200 housed inside may be slid into or pushed into the drilled hole 820. The implant pusher 812 may also move with the inserter tube 814 and remains close to or touching the proximal end of the implant. Repair suture 222 extends along an outer surface of inserter tube 814 and may be circumferentially spaced away from tension sutures 220 so as to minimize interference or disruption the suture tensioning.

Turning now to FIG. 8C, another cross section view is provided showing the subsequent step to FIG. 8B in the use of the tissue repair system 800. The implant assembly 200 is shown placed into the hole 820 in a coaxial orientation. This is achieved by retracting the inserter tube 814 in an axial direction so as to reveal the implant pusher 812 which remains adjacent the anchor proximal end. The implant pusher 812 may be fixed relative to a first portion of the handle (not shown here), while the inserter tube 814 may be attached at its proximal end to a moveable block coupled to a knob, slide, or trigger (not shown here) housed on a handle which can be activated by the user. Once the inserter tube 814 has been retracted to the outermost level of the bone, the implant is left inside the preformed hole, exposed to the bone as shown in FIG. 8C. Tension on the repair sutures 222 approximates tissue 224 to bone 822.

Once tissue is adjacent bone hole 820, tension sutures 220 may be tensioned as shown in FIG. 8D, with the implant pusher 812 remaining stationary within the bone space. The implant pusher 812 ideally extends into the bone to the bottom of the cortical layer, typically 0.02" to 0.05" below the bone/tissue surface. As the sutures 220 are tensioned, the implant 204 retracts upon itself with the end of the implant pusher 812 providing counter traction and assumes a shorted, expanded state with an increased effective diameter. By "counter traction," we mean a back stop is provided resisting movement of the proximal end of the implant proximally, thus causing the implant to bunch and expand. As the sutures 220 are tensioned, the at least one eyelet 218 may reduce in size, and/or be pulled into a distal opening of the anchor 204, and/or be pulled up against a closed distal end of implant 204 so as to lock the repair suture 222 relative to the anchor 204 and thereby the bone. Therefore before tensioning sutures 220, repair sutures free ends 222 may be withdrawn to as to better place soft tissue closer to bone. In addition, the inventors also envisions a partially deployed configuration (not shown here) wherein the tension sutures 220 are pulled so to partially tighten the knot 228 around repair sutures 222 and may also partially expand the soft anchor 204 radially, at which point ends of repair suture 222 may be further withdrawn to finely tune the position of the soft tissue 224 relative to the bone and implant assembly 200. For example radially expanding and axially contracting the anchor 204 may naturally move the knot 228 in a proximal direction, creating some slack in the repair suture 222 between the bone and the tissue 224, which may be compensated for with this fine tuning in a partial deployed configuration. Therefore partial deployment is defined as a knot configuration sufficient to allow the repair suture 222 to slide there through, and a partial anchor deployment that also allows the repair suture 222 to slide and adjust tension along the repair suture 222 and location of the soft tissue 224.

Expansion is accomplished primarily by the orientation change of the fibers as discussed earlier. When the anchor implant 204 increases in diameter, the soft anchoring implant becomes larger than the hole through which it was inserted in the cortical bone 822, thus resisting pull out. The soft anchoring implant 204 also embeds itself to some degree into the cancellous bone 824 that makes up the majority of the walls of the bone hole 820. This is possible because in most cases, the cancellous bone 824 is significantly softer than the associated cortical bone layer 822 above it. This "embedding" of the implant into the cancellous bone may also contribute to resistance of the implant to pull out. The soft anchoring implant assembly 200 is preferably placed into the bone in a lengthwise or axial orientation, such that one of the ends enters the bone first, with the opposite end entering last. Of note, repair sutures 222 that lie along the outer surface of anchor 204 will also be at least partially embedded into the bone as the anchor deploys, providing a supplemental repair suture lock means.

Figure 9:
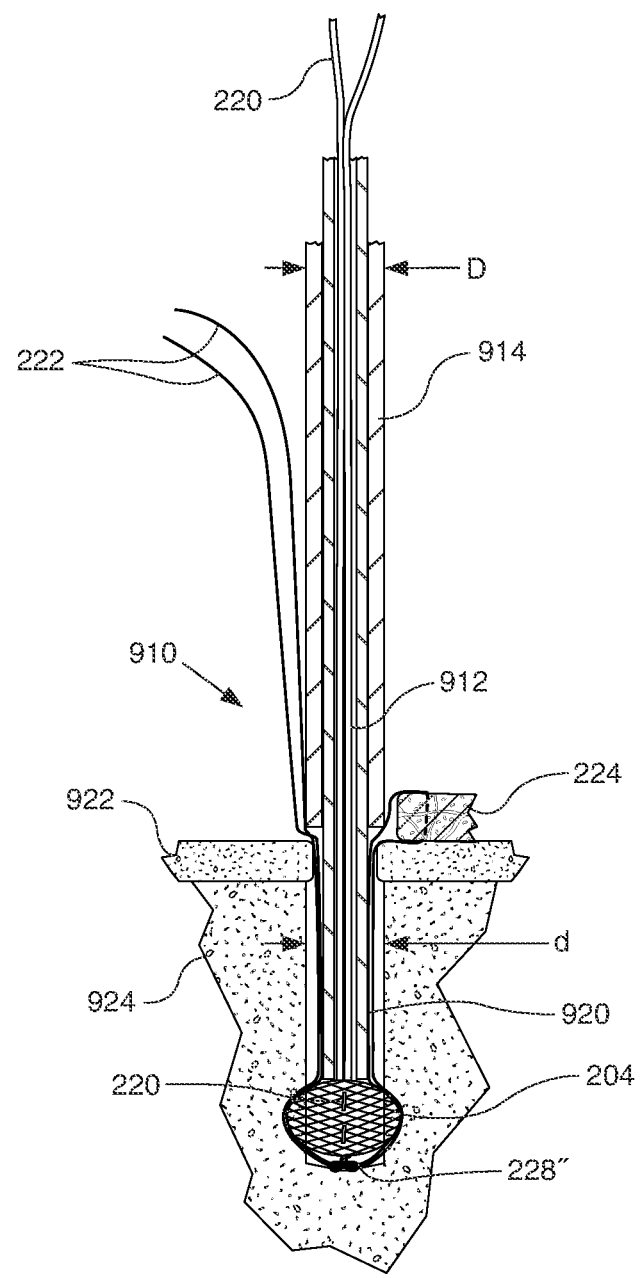
FIG. 9 illustrates an alternative system and method of tissue repair.

FIG. 9 shows an alternate embodiment, with an insertion tool 910 configured to place and deploy an anchor 204 towards a distal end of bone hole, and spaced distally away from the cortical bone layer 922. This may allow the bone hole 920 to have a smaller diameter than the assembly described in FIGS. 8A-8D, as inserter tube 914 is not configured to extend into the bone hole during operation. Diameter or width of outer tube "D" is larger than prepared bone hole width or diameter "d". Similar to the method described in FIGS. 8A, repair sutures have been coupled to the soft tissue and threaded through at least one eyelet 218. Repair sutures 222 may also be adjusted so as to slide through knot 228" and pull soft tissue 224 closer to bone hole 920. Inserter tool distal end 910 may then be placed adjacent to or against outer surface of bone. Push tube 912 may then engage a proximal end of anchor 204 so as to push anchor 204 into the bone hole, while the outer tube 914 remains stationary or is retracted, the push tube 912 extending to a location spaced distally from the harder cortical bone 922. Push tube 912 therefore extends distally from inserter tube end, as shown in FIG. 9 and at least partially into bone hole 920, beyond the cortical layer 922. Tension may be simultaneously applied to tension suture 220 as the push element 912 moves the anchor 204 distally, or these steps may be applied in a more serial or overlapping manner, to allow placement of anchor 204 before tightening knot 228" associated with tension suture 220. Anchoring is achieved by the radial expansion of the anchor 204, through orientation changes within the fibers, so that the anchor 204 embeds and or wedges into walls of the bone hole, the bone hole comprising softer cancellous bone 924 along this portion of the bone hole 920. The softer cancellous bone 924 may be at least partially displaced by the radially expanding anchor, creating a local pocket or cavity having a larger diameter to house the deployed anchor, preventing the anchor 204 from moving. Improved deployment with a strongly anchored assembly is accomplished as previously described by simultaneously applying both high tension to tension sutures 220 with either the end of the implant pusher 912 moving distally or at least providing counter traction and keeping the implant 204 at a distal location as shown. The implant 204 assumes a shorted, expanded state with an increased effective diameter. By "counter traction," we mean a back stop is provided resisting movement of the proximal end of the implant 204 proximally, thus causing the implant to bunch and expand. As the sutures 220 are tensioned, the at least one eyelet 218 may reduce in size, and/or be pulled into a distal opening of the anchor 204, and/or be pulled up against a closed distal end of implant 204 so as to lock the repair suture 222 relative to the anchor 204 and thereby the bone. Once deployed, the implant 204 is left in a distal location inside the preformed hole, exposed to the bone as shown in FIG. 9. This embodiment may help to reduce excessive slack in the repair suture 222 from occurring between the knot 228" and the soft tissue 224.

Figure 10A:
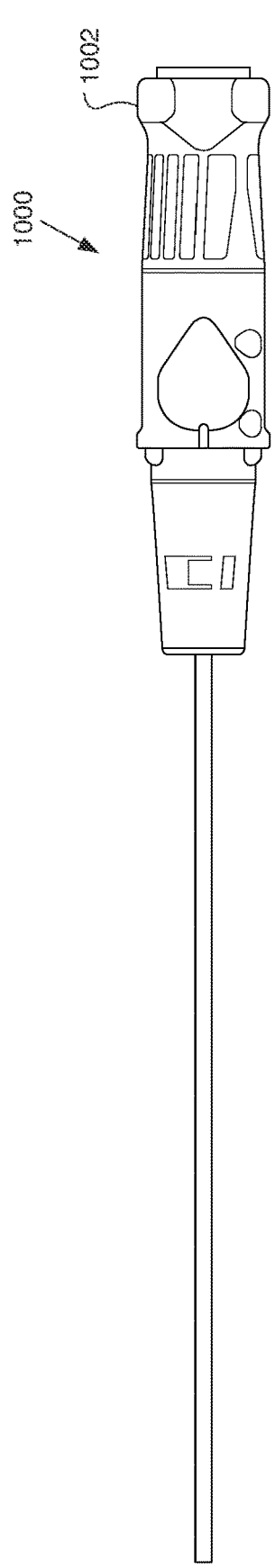
FIGS. 10A-10B illustrates an example handle of tissue repair systems.
Figure 10B:
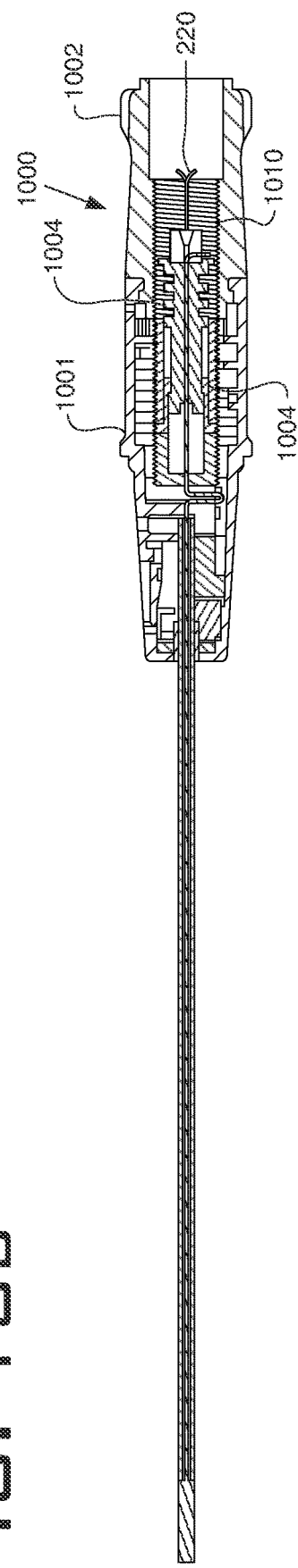

FIGS. 10A and 10B shows an exemplary delivery system of FIG. 8A-8C. Key to system is the ability to apply a controlled tension on the tension sutures 220. This tension applied to the sutures compresses the soft anchoring implant 204 and effects a change in orientation of the axially-aligned fibers or yarns to an orientation more orthogonal to the axis, thus enlarging the effective diameter of the implant 204. A distance X inherently applies a tensile force Y on the anchor 204 and is typically in the range of 0.2" to 2", the tensile force Y on the tension sutures 220 in turn creates an equal compressive force on the implant. A distance X will also inherently move knot 228 and/or may tighten knot 228. This tensile force Y is typically directly related to the travel distance X of element 1004, but also dependent upon the resistance of the tissue, stiffness of the sutures, etc. This tensile force Y is ideally in the range of 50N to 200N force in order to adequately tension the sutures 220 to create good retention of the implant 204, particularly in bony tissue. An optimal configuration may tension the sutures 220 while simultaneously tightening the knot 228, X being approximately a distance of approximately 0.4-1.8", corresponding to a tensile force in some tissue formations of about 140N. Alternatively, an inserter can be configured to apply a given force, regardless of distance travelled. For such embodiments, force could release due to a friction hold on the sutures, a breakaway tab, a measurement device, or another structure or force measurement device.

It is important to note that the sutures may also be tensioned by hand or with the use of some other tensioning mechanism. Tensioning sutures to a high force by hand can be difficult. Alternate mechanisms are described in U.S. Publication No. 2013/0123810 (Brown et al.), incorporated by reference herein.

FIG. 10B is a cross section of a tissue repair delivery system 1000 with an internally threaded shaft tensioning mechanism. In this embodiment, a rotatable knob 1002 is mounted on the back or proximal end of the handle 1001. A threaded block 1004 is mounted axially along the handle 1001, and is threadingly coupled to a cavity within a knob 1002. The knob 1002 includes internal female threads for receiving the threaded block 1004. The suture strands or tension suture 220 are attached to the threaded block 1004.

Rotation of the knob 1002, axially moves the threaded block 1004 proximally, pulling the suture strands with it. This axial movement tensions the tension sutures 220. The amount of travel can be limited, by stops or frangible portions (not shown) so as to provide the appropriate distance of pull and/or force on the tensions suture and also the knot 228.

While this disclosure has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting, the full scope rather being conveyed by the appended claims.

The invention claimed is:

1. A tissue repair assembly for knotlessly locking a repair tissue to a bone comprising:
   an anchoring implant formed of a suture material having a proximal end, a distal end, and a longitudinal axis extending therebetween;
   a first suture having a first length portion and a second length portion continuous with the first length portion, the first length portion coupled to the anchoring implant such that an end of the suture first length portion exits the anchoring implant proximal end, the second length portion formed in a knot having at least one eyelet; and
   a second suture;
   wherein tensioning the first length portion end is configured to change the anchoring implant from an elongate configuration to a deployed configuration;
   wherein tensioning the first length portion end is also configured to change the knot from an unlocked configuration that slidingly receives the second suture through the at least one eyelet to a locked configuration that locks the second suture and inhibits it from sliding therethrough.

2. The tissue repair assembly of claim 1 wherein tensioning the first length portion end is configured to simultaneously change the anchoring implant to the deployed configuration and the knot to the locked configuration.

3. The tissue repair assembly of claim 1 wherein tensioning the first length portion end to change the anchoring implant to the deployed configuration and the knot to the locked configuration defines a final knotless repaired configuration and in the final knotless repaired configuration, the first suture is coupled to the anchoring implant and the knot is fixed in place relative to the anchoring implant.

4. The tissue repair assembly of claim 1 wherein the first length portion is coupled to the anchoring implant via repeated interweaving through a wall of the anchoring implant.

5. The tissue repair assembly of claim 1 wherein the knot is external to the anchoring implant and is configured such that tensioning the first length portion end changes the configuration of the knot and also draws the knot against but external to a lumen of the anchoring implant.

6. The tissue repair assembly of claim 1, wherein the knot is a locking knot.

7. The tissue repair assembly of claim 1, further comprising a suture passer, disposed through the at least one eyelet, configured to draw the second suture therethrough.

8. The tissue repair assembly of claim 1 further comprising a tissue repair delivery system operatively coupled to the first length portion end for tensioning the first length portion end to increase a locking force of the lock between the second suture and the knot.

9. The tissue repair assembly of claim 1 wherein the at least one eyelet includes a plurality of eyelets formed in a spiral.

10. The tissue repair assembly of claim 1 wherein the at least one eyelet is wrapped around a tubular shaft in the unlocked configuration.

11. A tissue repair assembly for knotlessly locking a first tissue to a second tissue comprising:
    an anchoring implant formed of a suture material having a proximal end, a distal end, and a longitudinal axis extending therebetween;
    a first suture having a first length portion and a second length portion continuous with the first length portion, the first length portion coupled to the anchoring implant such that an end of the suture first length portion exits the anchoring implant proximal end, the second length portion formed in a knot having at least one eyelet; and
    a second suture;
    wherein tensioning the first length portion end is configured to change the anchoring implant from an elongate configuration to a deployed configuration;
    wherein tensioning the first length portion end is configured to change the knot from an unlocked configuration that slidingly receives the second suture through the at least one eyelet to a locked configuration that locks the second suture and inhibits it from sliding therethrough, the knot remaining in a fixed location relative to the anchoring implant during tensioning.

12. The tissue repair assembly of claim 11 wherein tensioning the first length portion end is configured to simultaneously change the anchoring implant to the deployed configuration and the knot to the locked configuration.

13. The tissue repair assembly of claim 11 wherein tensioning the first length portion end to change the anchoring implant to the deployed configuration and the knot to the locked configuration defines a final knotless repaired configuration and in the final knotless repaired configuration, the first suture is coupled to the anchoring implant and the knot is drawn against the anchoring implant.

14. The tissue repair assembly of claim 11 wherein the first length portion is coupled to the anchoring implant via repeated interweaving through a wall of the anchoring implant.

15. The tissue repair assembly of claim 11 wherein the knot is external to the anchoring implant and the knot is configured such that tensioning the first length portion end changes the configuration of the knot and retains the knot against but external to a lumen of the anchoring implant.

16. The tissue repair assembly of claim 11, wherein the knot is a locking knot.

17. The tissue repair assembly of claim 11, further comprising a suture passer, disposed through the at least one eyelet, configured to draw the second suture therethrough.

18. The tissue repair assembly of claim 11 further comprising a tissue repair delivery system operatively coupled to the first length portion end for tensioning the first length portion end and increase a locking force of the lock between the second suture and the knot.

19. The tissue repair assembly of claim 11 wherein the at least one eyelet includes a plurality of eyelets formed in a spiral.

20. The tissue repair assembly of claim 11 wherein the at least one eyelet is wrapped around a tubular shaft in the unlocked configuration.

* * * * *